US010285788B2

(12) United States Patent
Bosman et al.

(10) Patent No.: US 10,285,788 B2
(45) Date of Patent: May 14, 2019

(54) ACTUATOR WITH GROUPED MAGNETS FOR PERSONAL CARE APPLIANCE

(71) Applicant: KONINKLIJKE PHILIPS N.V., Eindhoven (NL)

(72) Inventors: Franciscus Jozef Bosman, Drachten (NL); Pieter Johannes Bax, Drachten (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 316 days.

(21) Appl. No.: 15/108,715

(22) PCT Filed: Dec. 22, 2014

(86) PCT No.: PCT/IB2014/067203
§ 371 (c)(1),
(2) Date: Jun. 28, 2016

(87) PCT Pub. No.: WO2015/101898
PCT Pub. Date: Jul. 9, 2015

(65) Prior Publication Data
US 2016/0324611 A1 Nov. 10, 2016

Related U.S. Application Data

(60) Provisional application No. 61/921,685, filed on Dec. 30, 2013.

(51) Int. Cl.
*A61C 17/34* (2006.01)
*H02K 33/16* (2006.01)
(Continued)

(52) U.S. Cl.
CPC ........ *A61C 17/3472* (2013.01); *A61C 17/225* (2013.01); *A61C 17/3418* (2013.01);
(Continued)

(58) Field of Classification Search
CPC ............ A61C 17/3418; A61C 17/3445; A61C 17/225; A61C 17/3472; A61C 1/06; H02K 2201/18; H02K 33/00; H02K 33/16
(Continued)

(56) References Cited

U.S. PATENT DOCUMENTS 6,727,617 B2  4/2004  McMullen et al.
2001/0026204 A1  10/2001  Petro
(Continued)

FOREIGN PATENT DOCUMENTS

CN   101248568 A   8/2008
CN   101554342 A   10/2009
(Continued)

*Primary Examiner* — Alex W Mok (57) ABSTRACT

Actuator for a personal care appliance comprising a housing, a spindle, a tangential actuator portion, an axial actuator portion, and a controller. The tangential actuator portion comprises a first magnet and pole assembly having a first sequence of individual grouped magnet segments spaced apart within the housing in a first radial orientation and polarity order, and a first pole assembly of pole members in a first radial configuration about the spindle, a second magnet and pole assembly having a second sequence of individual grouped magnet segments spaced apart within the housing in a second radial orientation and polarity order, and a second pole assembly of pole members in a second radial configuration about the spindle, and an electromagnetic coil disposed about the spindle in-between the first and second magnet and pole assemblies. The tangential actuator portion rotationally displaces the spindle with respect to the housing about a principal axis.

14 Claims, 8 Drawing Sheets

(51) Int. Cl.
*A61C 17/22* (2006.01)
*H02K 33/00* (2006.01)
*A61C 1/06* (2006.01)

(52) U.S. Cl.
CPC ......... *A61C 17/3445* (2013.01); *H02K 33/00* (2013.01); *H02K 33/16* (2013.01); *A61C 1/06* (2013.01); *H02K 2201/18* (2013.01)

(58) Field of Classification Search
USPC .......................................................... 310/20
See application file for complete search history.

(56) References Cited

U.S. PATENT DOCUMENTS

| | | | |
|---|---|---|---|
| 2009/0070948 A1 | 3/2009 | Bax | |
| 2011/0005015 A1 | 1/2011 | Iwahori et al. | |
| 2012/0001499 A1* | 1/2012 | Makino | ................. H02K 41/03 310/12.14 |
| 2012/0043832 A1* | 2/2012 | Neff | ................... H02K 41/0356 310/12.14 |
| 2012/0262259 A1* | 10/2012 | Teo | ........................ H02K 16/00 335/296 |

FOREIGN PATENT DOCUMENTS

| | | |
|---|---|---|
| CN | 102460917 A | 5/2012 |
| CN | 102714443 A | 10/2012 |
| FR | 1218671 | 5/1960 |
| GB | 2310499 A | 8/1997 |
| RU | 2006119443 A | 12/2007 |
| RU | 2444326 C1 | 3/2012 |
| WO | 9923744 A1 | 5/1999 |
| WO | 2004047670 A1 | 6/2004 |
| WO | 2005046507 A1 | 5/2005 |
| WO | 2007021310 A1 | 2/2007 |
| WO | 2010143156 A1 | 12/2010 |
| WO | 2011055227 A2 | 5/2011 |
| WO | 2012042427 A2 | 4/2012 |

* cited by examiner

Radial
magnetization
pattern

FIG. 9

Parallel
magnetization
pattern

FIG. 10

ACTUATOR WITH GROUPED MAGNETS FOR PERSONAL CARE APPLIANCE

CROSS-REFERENCE TO PRIOR APPLICATIONS

This application is the U.S. National Phase application under 35 U.S.C. § 371 of International Application No. PCT/IB2014/067203, filed on Dec. 22, 2014, which claims the benefit of U.S. Provisional Patent Application No. 61/921,685, filed on Dec. 30, 2013. These applications are hereby incorporated by reference herein.

The present embodiments relate generally to drive systems for a personal care appliance, such as a power toothbrush, and more particularly, to a combined tangential and axial motion drive system featuring individual N-S grouped magnet segments.

A tangential actuator generally comprises a resonant system in which a spring function is delivered by an electromagnetic system of (i) small magnets mounted on the inside of a metal can or cylindrical housing and (ii) poles mounted on a shaft within the metal can. In addition, a cogging position of the poles (i.e., rotor) has a spring characteristic when rotating the shaft. Still further, the known tangential actuator has evenly distributed north (N) and south (S) magnets and poles.

The above-mentioned tangential actuator has a few characteristics that hamper its industrialization into a product. That is, it has a relatively large number of permanent magnets that must be mounted on the inside of the metal can or cylindrical housing. For example, a four (4) pole tangential actuator would require sixteen (16) pieces of permanent magnets, and for a five (5) pole tangential actuator, twenty (20) pieces of permanent magnets would be required. As a result, such a large number of permanent magnet parts, especially in the context of actuators for small personal care appliances, render the manufacturing in large quantities thereof to be complex and expensive. In other words, an actuator having many permanent magnet parts drives up cost and manufacturing complexity undesirably.

With the most common and low priced high magnet grade permanent magnets, a low-end personal care product, or electric toothbrush, with an operating frequency around 260 Hz, and with a sufficient strong actuator to drive the brushing process, is inherently not possible. In addition, lowering a stiffness of the tangential actuator by reducing the magnet strength undesirably reduces the motor constant of the actuator, thereby disadvantageously creating a weaker actuator. Furthermore, reducing the actuator stiffness by reducing an overlap of pole and permanent magnet undesirably reduces the inertia of the rotor, which results in still a too high resonance frequency. The only way to reduce the operating frequency of the actuator and keep the same actuator strength would be adding a part just for inertia to reduce the resonance frequency independent of the actuator configuration.

Accordingly, an improved method and apparatus for overcoming the problems in the art is desired.

According to one aspect of the embodiments of the present disclosure, permanent magnets are grouped in pairs, i.e., including groups of magnets in pairs (i.e., individual N-S or S-N grouped magnet segments as discussed herein), to advantageously reduce the number of magnets required in an actuator by a factor of two (2). In addition, as a result of grouping magnets in pairs, the inertia increases at the same angular stiffness, enabling to lower the resonance without lowering (i) the stiffness and (ii) motor constant of the actuator. For an axial actuator, using pairs of permanent magnets (i.e., individual N-S or S-N grouped magnet segments as discussed herein) advantageously reduces the number of magnets for a two-pole (2-pole) axial actuator by twenty-five percent (25%).

According to one embodiment, an actuator for a personal care appliance comprises a housing, a spindle, and at least a tangential actuator portion. The actuator further comprises a controller for providing at least one of a rotation control signal, a translation control signal, and/or any combination of rotation and translation control signals. The personal care appliance can comprise an electric toothbrush, an oral hygiene device, a tooth polishing device, and any combination thereof.

The housing comprises magnetic material having an inner radial surface and a principal axis extending longitudinally along a length dimension thereof. The housing further includes at least first and second portions along the length dimension thereof. The spindle comprises magnetizable material extending longitudinally within the housing along the principal axis of the housing. The spindle further includes at least first and second portions corresponding with the at least first and second portions of the housing, respectively. The tangential actuator portion is coupled between the first portion of the housing and the first portion of the spindle.

The tangential actuator portion comprises (i) a first permanent magnet and pole assembly, (ii) a second permanent magnet and pole assembly, and (iii) an electromagnetic coil winding disposed about and coupled to the spindle in-between the first and second magnet and pole assemblies.

The first permanent magnet and pole assembly of the tangential actuator comprises (i)(a) a first sequence of individual N-S grouped magnet segments spaced apart in a first radial orientation and having a first polarity order, each individual N-S grouped magnet segment of the first sequence being longitudinally disposed along the inner radial surface within the first portion of the housing. The first permanent magnet and pole assembly of the tangential actuator further comprises (i)(b) a first pole assembly having pole members arranged in a first radial configuration disposed about the spindle on the first portion of the spindle.

The second permanent magnet and pole assembly of the tangential actuator comprises (ii)(a) a second sequence of individual N-S grouped magnet segments spaced apart in a second radial orientation and having a second polarity order, opposite to the first polarity order, each individual N-S grouped magnet segment of the second sequence being longitudinally disposed along the inner radial surface within the first portion of the housing. The second permanent magnet and pole assembly further comprises (ii)(b) a second pole assembly having pole members arranged in a second radial configuration disposed about the spindle on the first portion of the spindle.

In operation, the tangential actuator portion rotationally displaces the spindle with respect to the housing about the principal axis in response to a rotation control signal applied to the electromagnetic coil via the controller.

In another embodiment, each individual N-S grouped magnet segment of the first and second sequence of individual N-S grouped magnet segments comprises a single magnet segment having a N-S magnetization pattern. In a further embodiment, the N-S magnetization pattern comprises a radial magnetization pattern. In a yet further embodiment, the N-S magnetization pattern comprises a parallel magnetization pattern.

In yet another embodiment, the first pole assembly of the tangential actuator portion is configured for operation between two distinct, different cogging positions determined as a function of the first sequence of individual N-S grouped magnet segments. In addition, the second pole assembly of the tangential actuator portion is configured for operation between two distinct, different cogging positions determined as a function of the second sequence of individual N-S grouped magnet segments. Furthermore, in one embodiment, the two distinct, different cogging positions of the second pole assembly are in radial alignment with the two distinct, different cogging positions of the first pole assembly. Still further, in another embodiment, the two distinct, different cogging positions of the second pole assembly are in radial non-alignment with the two distinct, different cogging positions of the first pole assembly.

In still another embodiment, the second radial orientation of the second sequence of individual N-S grouped magnet segments is offset from the first radial orientation of the first sequence of individual N-S grouped magnet segments, and the second radial configuration of the second pole assembly is offset from the first radial configuration of the first pole assembly.

In another embodiment, the actuator further comprises an axial actuator portion coupled between the second portion of the housing and the second portion of the spindle. The axial actuator portion comprises (i) a third permanent magnet and pole assembly, (ii) a fourth permanent magnet and pole assembly, and (iii) a second electromagnetic coil winding disposed about and coupled to the spindle in-between the third and fourth magnet and pole assemblies.

The third magnet and pole assembly of the axial actuator portion comprises (i)(a) a third sequence of magnet segments spaced apart in a first longitudinal orientation and having a third polarity order, each segment of the third sequence of magnet segments being circumferentially disposed about the inner radial surface within the second portion of the housing. The third magnet and pole assembly of the axial actuator portion further comprises (i)(b) a third pole assembly having at least one pole member disposed about the spindle on the second portion of the spindle.

The fourth magnet and pole assembly of the axial actuator portion comprises (ii)(a) a fourth sequence of magnet segments spaced apart in a second longitudinal orientation and having a fourth polarity order, opposite to the third polarity order, each segment of the fourth sequence of magnet segments being circumferentially disposed about the inner radial surface within the second portion of the housing. The fourth magnet and pole assembly of the axial actuator portion further comprises (ii)(b) a fourth pole assembly having at least one pole member disposed about the spindle on the second portion of the spindle.

In operation, the axial actuator portion axially displaces the spindle with respect to the housing along the principal axis in response to a translation control signal applied to the second electromagnetic coil via the controller.

In another embodiment, at least one segment of the third sequence of magnet segments further comprises a number of sub-segments of a same polarity spaced apart about a given circumference of the inner radial surface. In addition, at least one segment of the fourth sequence of magnet segments further comprises a number of sub-segments of a same polarity spaced apart about a second given circumference of the inner radial surface. In one embodiment, the number of sub-segments of the third sequence of magnet segments comprises four sub-segments, wherein the four sub-segments are equally spaced apart from one another about the given circumference. In addition, the number of sub-segments of the fourth sequence of magnet segments comprises four sub-segments, wherein the four sub-segments are equally spaced apart from one another about the second given circumference.

In yet another embodiment, the third sequence of magnet segments further includes at least one individual N-S grouped magnet segment intermediate a first and last magnet segment in the third sequence of magnet segments, wherein the third pole assembly further comprises at least two pole members disposed about the spindle on the second portion of the spindle. The fourth sequence of magnet segments further includes at least one individual N-S grouped magnet segment intermediate a first and last magnet segment in the fourth sequence of magnet segments, wherein the fourth pole assembly further comprises at least two pole members disposed about the spindle on the second portion of the spindle. In another embodiment, the at least two pole members of the third pole assembly have axial cogging positions determined as a function of a position of the at least one individual N-S grouped magnet segment in the third sequence of magnet segments, and the at least two pole members of the fourth pole assembly have axial cogging positions determined as a function of a position of the at least one individual N-S grouped magnet segment in the fourth sequence of magnet segments.

In still another embodiment, an actuator for a personal care appliance comprises (a) a cylindrical housing of magnetic material having an inner radial surface and a principal axis extending longitudinally along a length dimension thereof, the housing further including at least first and second portions along the length dimension thereof; (b) a spindle of magnetizable material extending longitudinally within the housing along the principal axis of the housing, the spindle further including at least first and second portions corresponding with the at least first and second portions of the housing, respectively; and (c) a tangential actuator portion coupled between the first portion of the housing and the first portion of the spindle. The personal care appliance comprises one selected from the group consisting of an electric toothbrush, an oral hygiene device, a tooth polishing device, and any combination thereof.

The tangential actuator portion comprises (i) a first permanent magnet and pole assembly, wherein the first permanent magnet and pole assembly of the tangential actuator comprises (i)(a) a first sequence of individual N-S grouped magnet segments spaced apart in a first radial orientation and having a first polarity order, each individual N-S grouped magnet segment of the first sequence being longitudinally disposed along the inner radial surface within the first portion of the housing, and (i)(b) a first pole assembly having pole members arranged in a first radial configuration disposed about the spindle on the first portion of the spindle, (ii) a second permanent magnet and pole assembly, wherein the second permanent magnet and pole assembly of the tangential actuator comprises (ii)(a) a second sequence of individual N-S grouped magnet segments spaced apart in a second radial orientation and having a second polarity order, opposite to the first polarity order, each individual N-S grouped magnet segment of the second sequence being longitudinally disposed along the inner radial surface within the first portion of the housing, and (ii)(b) a second pole assembly having pole members arranged in a second radial configuration disposed about the spindle on the first portion of the spindle, and (iii) an electromagnetic coil winding disposed about and coupled to the spindle in-between the first and second magnet and pole assemblies, wherein responsive to a rotation control signal applied to the electromagnetic coil, the tangential actuator portion rotationally displaces the spindle with respect to the housing about the principal axis.

The actuator for the personal care appliance further comprises (d) an axial actuator portion coupled between the second portion of the housing and the second portion of the spindle. The axial actuator portion comprises (i) a third permanent magnet and pole assembly, wherein the third magnet and pole assembly of the axial actuator portion comprises (i)(a) a third sequence of magnet segments spaced apart in a first longitudinal orientation and having a third polarity order, each segment of the third sequence of magnet segments being circumferentially disposed about the inner radial surface within the second portion of the housing, and (i)(b) a third pole assembly having at least one pole member disposed about the spindle on the second portion of the spindle. The axial actuator portion further comprises (ii) a fourth permanent magnet and pole assembly, wherein the fourth magnet and pole assembly of the axial actuator portion comprises (ii)(a) a fourth sequence of magnet segments spaced apart in a second longitudinal orientation and having a fourth polarity order, opposite to the third polarity order, each segment of the fourth sequence of magnet segments being circumferentially disposed about the inner radial surface within the second portion of the housing, and (ii)(b) a fourth pole assembly having at least one pole member disposed about the spindle on the second portion of the spindle. The axial actuator portion still further comprises (iii) a second electromagnetic coil winding disposed about and coupled to the spindle in-between the third and fourth magnet and pole assemblies, wherein responsive to a translation control signal applied to the second electromagnetic coil, the axial actuator portion axially displaces the spindle with respect to the housing along the principal axis.

The actuator for the personal care appliance still further comprises (e) a controller for providing at least one selected from the group consisting of the rotation control signal, the translation control signal, and any combination of both rotation and translation control signals. In a further embodiment, each individual N-S grouped magnet segment of the first and second sequence of individual N-S grouped magnet segments comprises a single magnet segment having a N-S magnetization pattern, and wherein the N-S magnetization pattern comprises one selected from the group consisting of a radial magnetization pattern and a parallel magnetization pattern.

In yet another embodiment, the third sequence of magnet segments further includes at least one individual N-S grouped magnet segment intermediate a first and last magnet segment in the third sequence of magnet segments. The third pole assembly further comprises at least two pole members disposed about the spindle on the second portion of the spindle. Still further, the at least two pole members have axial cogging positions determined as a function of a position of the at least one individual N-S grouped magnet segment in the third sequence of magnet segments. In addition, the fourth sequence of magnet segments further includes at least one individual N-S grouped magnet segment intermediate a first and last magnet segment in the fourth sequence of magnet segments. The fourth pole assembly further comprises at least two pole members disposed about the spindle on the second portion of the spindle. Still further, the at least two pole members have axial cogging positions determined as a function of a position of the at least one individual N-S grouped magnet segment in the fourth sequence of magnet segments.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to one aspect of the present embodiments, the grouping of magnets in pairs (i.e., individual N-S or S-N grouped magnet segments as discussed herein), halves the number of magnets in a tangential actuator, and creates higher inertia in the shaft or spindle, i.e., keeping the same functional stiffness by maintaining the angular overlap of pole and magnet. In the case of an axial actuator, the benefit is 25% for a two-pole (2-pole) axial actuator.

For a tangential actuator according to the embodiments of the present disclosure, the magnets include segments with magnetization patterns that create a radial oriented N and S part next to each other. In addition, a pole angle of the tangential actuator is increased until a desired magnet-pole overlap is created. This leads to several advantages. One advantage is that the actuator comprises fewer parts of magnets. Another advantage is that the actuator has an increased inertia without using an extra part. For instance, with respect to the tangential actuator portion as discussed herein, the pole sides shift with respect to the paired N and S magnet part outward, thus increasing the pole angle and the inertia. One additional benefit is that there are two sets of cogging positions with different characteristics, which could be advantageously used for creating two different functions in the personal care product.

Figure 1:
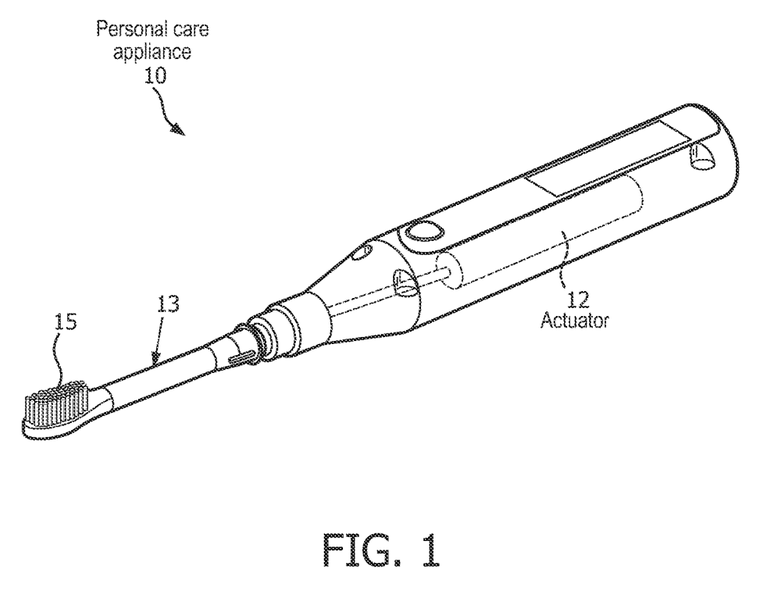
FIG. 1 is a perspective view of a personal care appliance that includes an actuator according to an embodiment of the present disclosure.

FIG. 1 is a perspective view of a personal care appliance 10 that includes a drive system that includes an actuator 12 according to an embodiment of the present disclosure. In one embodiment, the personal care appliance 10 comprises a power toothbrush. The actuator 12 is generally disposed within a handle of the personal care appliance 10. The actuator 12 uses magnetic action to drive an output mounting shaft 13 on which is mounted a workpiece 15, for example, a brushhead for the power toothbrush.

Figure 2:
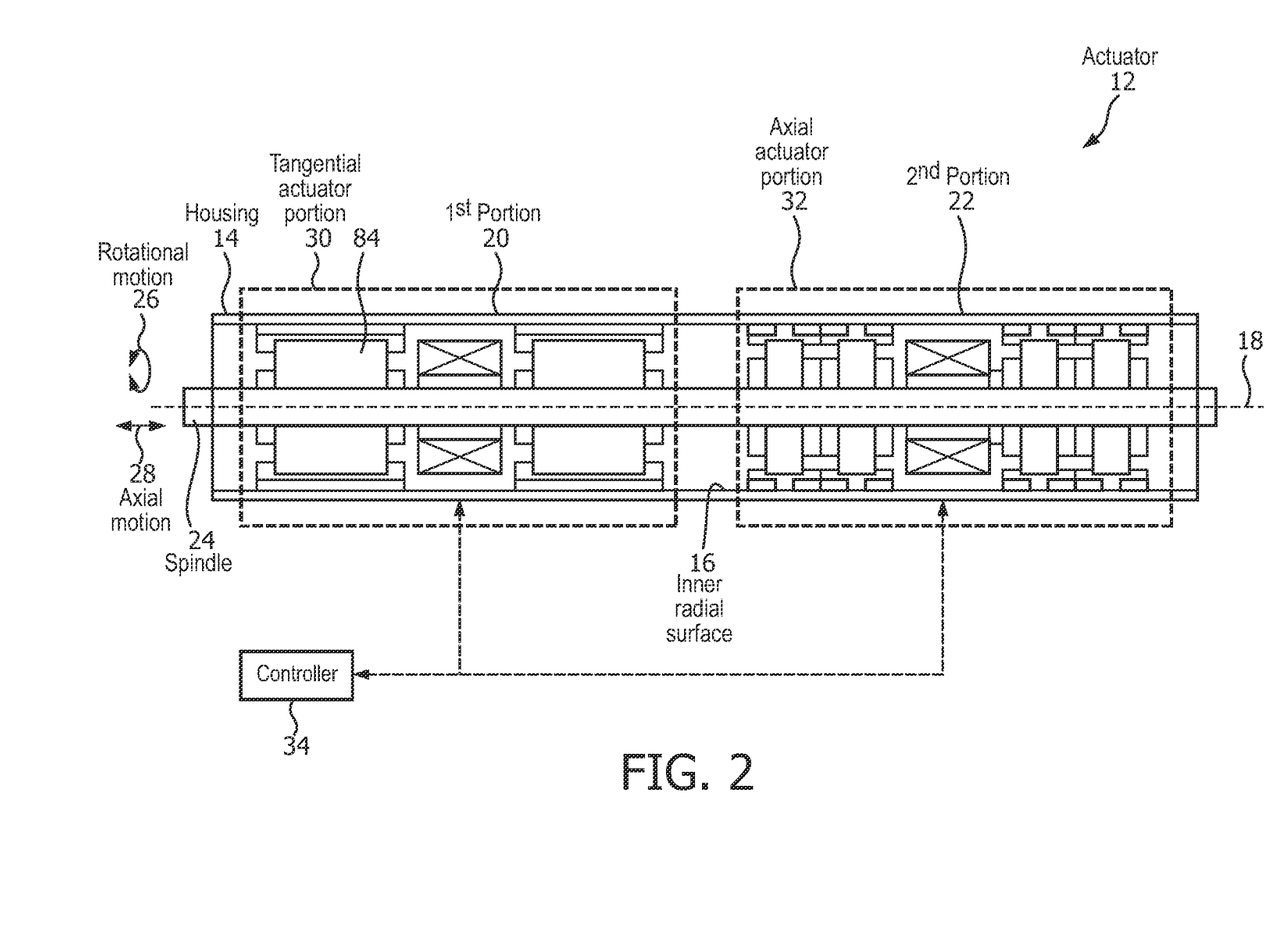
FIG. 2 is a schematic view of an actuator according to an embodiment of the present disclosure.

FIG. 2 is a schematic view of the actuator 12 according to an embodiment of the present disclosure, in greater detail. Actuator 12 comprises a cylindrical housing 14 of magnetic material having an inner radial surface 16 and a principal axis 18 extending longitudinally along a length dimension thereof. The housing 14 also includes at least first and second portions, indicated by referenced numerals 20 and 22, respectively, along the length dimension thereof. The actuator further comprises a spindle 24 of magnetizable material extending longitudinally within the housing 14 along the principal axis 18 of the housing. The spindle also includes at least first and second portions corresponding with the at least first and second portions 20 and 22, respectively, of the housing 14. Spindle 24 is mechanically coupled, via bearings or other suitable means known in the art, with respect to the housing 14. As a result, spindle 24 is enabled for both a rotational motion 26 and an axial motion 28 of the spindle with respect to the housing 14.

Actuator 12 further comprises a tangential actuator portion 30 and an axial actuator portion 32. The tangential actuator portion 30 is coupled between the first portion 20 of the housing 14 and the corresponding first portion of the spindle 24, whereas the axial actuator portion 32 is coupled between the second portion 22 of the housing 14 and the corresponding second portion of the spindle 24. The tangential actuator portion 30 will be discussed further herein below with reference to FIGS. 4-6. Similarly, the axial actuator portion 32 will be discussed further herein with reference to FIGS. 7 and 8.

With reference still to FIG. 2, actuator 12 further comprises a controller 24, wherein the controller includes any suitable microprocessor, microprocessors, controller, controllers, or other type of suitable control device known in the art. In particular, controller 34 is configured for providing at least one selected from the group consisting of (i) a rotation control signal to the tangential actuator portion 30, (ii) a translation control signal to the axial actuator portion 32, and (iii) any combination of both rotation and translation control signals, according to the particular requirements of a given actuator implementation. For example, the rotation and translation control signals can be configured to provide multiple different actuator motions and/or operational modes for the personal care appliance 10.

Figure 3:
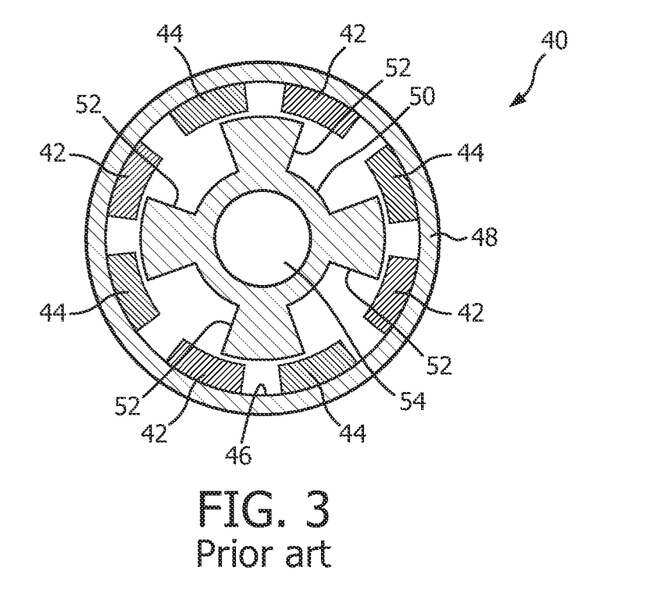
FIG. 3 is a cross-sectional view of a magnet and pole assembly of a tangential actuator according to prior art.

With reference now to FIG. 3, a cross-sectional view of a magnet and pole assembly 40 of a portion of a tangential actuator according to the prior art is shown. As illustrated, the prior art magnet and pole assembly 40 of the tangential actuator includes a plurality of N-polarity and S-polarity magnets indicated by reference numerals 42 and 44, respectively. The plurality of N-polarity and S-polarity magnets comprises eight (8) magnets of equal dimension, and equally spaced apart (i.e., an equi-gapped N magnet and S magnet arrangement), about an inner radial surface 46 of housing 48. Each N-polarity magnet 42 and S-polarity magnet 44 is further longitudinally disposed on the inner radial surface 46 of the housing 48, that is, directed perpendicularly into the page of the drawing figure. The magnet and pole assembly 40 further includes a pole assembly 50 having four (4) pole members, indicated by reference numeral 52, of equal dimension and equally spaced apart in a radial configuration disposed about a spindle 54. In this configuration, there prior art tangential actuator has one effective cogging position that provides a single tangential actuator characteristic.

Figure 4:
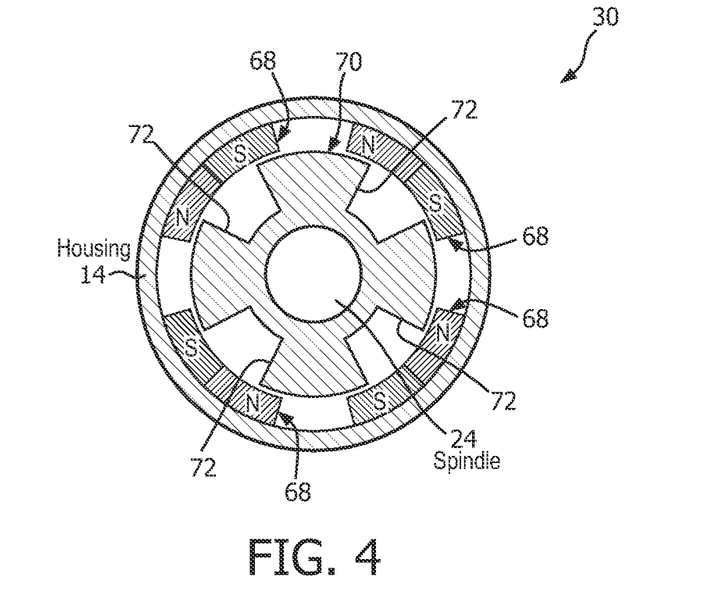
FIG. 4 is a cross-sectional view of a magnet and pole assembly of a tangential actuator portion, shown in a first distinct cogging position, of the actuator according to one embodiment of the present disclosure.
Figure 5:
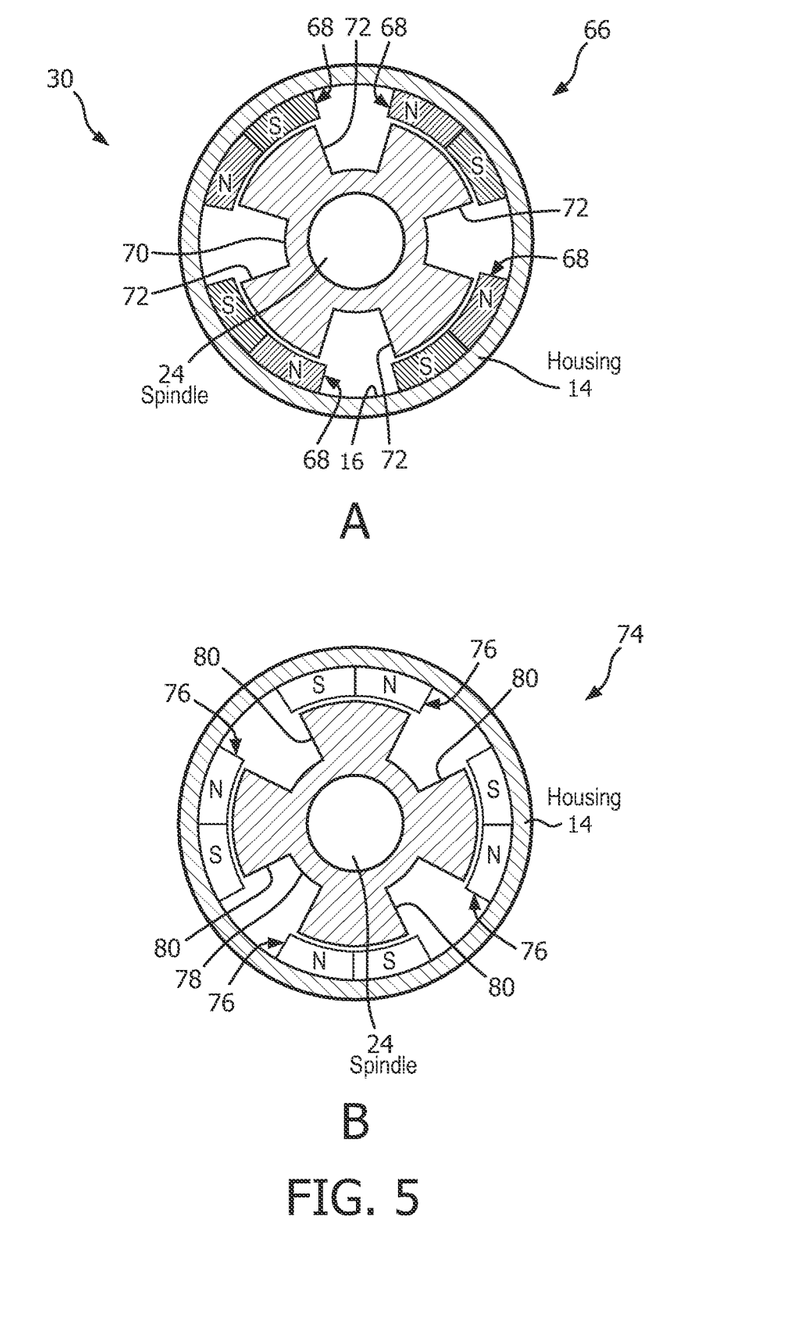
FIG. 5 comprises first and second cross-sectional views of (A) a first magnet and pole assembly, shown in a second distinct cogging position, and (B) a second magnet and pole assembly, respectively, of the tangential actuator portion of the actuator according to an embodiment of the present disclosure.
Figure 6:
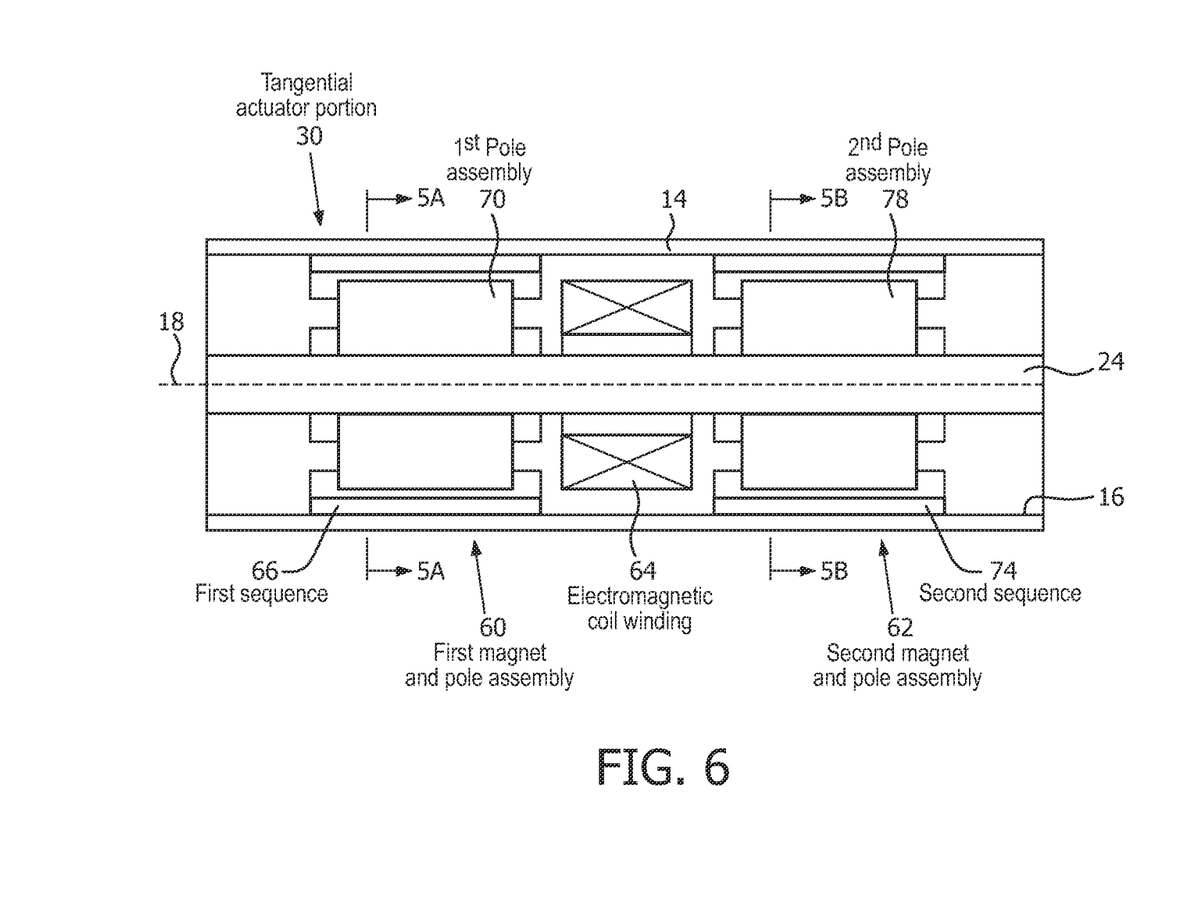
FIG. 6 is a cross-sectional view of the tangential actuator portion, along its length dimension, of the actuator according to an embodiment of the present disclosure.

In contrast, with reference now to FIGS. 4, 5 and 6, and as indicated earlier herein, the tangential actuator portion 30 of actuator 12 according to one embodiment of the present disclosure is coupled between the first portion 20 of the housing 14 and the corresponding first portion of the spindle 24. The tangential actuator portion 30 comprises (i) a first permanent magnet and pole assembly 60, (ii) a second permanent magnet and pole assembly 62 and (iii) an electromagnetic coil 64 (or electromagnetic coil winding). In addition, FIG. 4 illustrates a cross-sectional view of the first permanent magnet and pole assembly 60 (FIG. 6) of the tangential actuator portion 30, shown in a first distinct cogging position, of the actuator according to one embodiment of the present disclosure. FIG. 5 illustrates first and second cross-sectional views of (A) the first magnet and pole assembly 60 (FIG. 6), shown in a second distinct cogging position, and (B) a second magnet and pole assembly 62 (FIG. 6), respectively, of the tangential actuator portion 30 of the actuator 12 according to an embodiment of the present disclosure. Furthermore, FIG. 6 illustrates a cross-sectional view of the tangential actuator portion 30, along its length dimension, of the actuator 12.

The first permanent magnet and pole assembly 60 of the tangential actuator portion 30 comprises (i)(a) a first sequence 66 of individual N-S grouped magnet segments 68 spaced apart in a first radial orientation and having a first polarity order. The first radial orientation having a first polarity order can include, for example, a first individual N-S grouped magnet segment, a free space, a second individual N-S grouped magnet segment, a second free space, etc., until an $n_1^{th}$ individual N-S grouped magnet segment, and $n_1^{th}$ free space, where "$n_1$" is an integer number. As shown in FIG. 4, the integer number $n_1$ is equal to 4 (i.e., $n_1$=4) in one embodiment, further wherein the radial orientation comprises ninety degrees between the centers of adjacent ones of the individual N-S grouped magnet segments. However, "$n_1$" can represent any reasonable number of individual N-S grouped magnet segments configured for a given tangential actuator portion implementation. For example, "$n_1$" could be equal to 5 (i.e., $n_1$=5). In addition, each individual N-S grouped magnet segment 68 of the first sequence 66 is longitudinally disposed along the inner radial surface 16 within the first portion 20 of the housing 14, i.e., directed perpendicularly into the page of the drawing figure.

The first permanent magnet and pole assembly 60 of the tangential actuator portion 30 further comprises (i)(b) a first pole assembly 70 having a first set of pole members 72 arranged in a first radial configuration disposed about the spindle 24 on the corresponding first portion of the spindle. The first set of pole members 72 in the first radial configuration can include for example, a number of "$m_1$" poles, where "$m_1$" is an integer number. In one embodiment, the value of "$m_1$"="$n_1$" of the first sequence of individual N-S grouped magnet segments.

In addition, a free end radial surface of each pole member 72 of the first pole assembly 70 extends radially outward towards an inner radial surface of the first sequence 66 of individual N-S grouped magnet segments 68, proximate to, but separated by a gap from, the inner radial surface of the first sequence 66 of individual N-S grouped magnet segments 68. Still further, in one embodiment, the outer radial surface of each pole member 72 complements an inner radial surface of an individual N-S grouped magnet segment 68, for example, as shown in FIG. 5(A).

The second permanent magnet and pole assembly 62 of the tangential actuator portion 30 is similar to that of the first permanent magnet and pole assembly 60 with the following differences. The second permanent magnet and pole assembly 62 comprises (ii)(a) a second sequence 74 of individual S-N grouped magnet segments 76 spaced apart in a second radial orientation and having a second polarity order, opposite to the first polarity order. The second radial orientation and second polarity order can include, for example, a first individual S-N grouped magnet segment, a free space, a second individual S-N grouped magnet segment, a second free space, etc., until an $n_2^{th}$ individual S-N grouped magnet segment, and $n_2^{th}$ free space, where "$n_2$" is an integer number. As shown in FIG. 5(B), the integer number $n_2$ is equal to 4 (i.e., $n_2$=4) in one embodiment, further wherein the radial orientation comprises ninety degrees between the centers of adjacent ones of the individual S-N grouped magnet segments. However, "$n_2$" can represent any reasonable number of individual S-N grouped magnet segments configured for a given actuator implementation. For example, "$n_2$" could be equal to 5 (i.e., $n_2$=5). In addition, each individual S-N grouped magnet segment of the second sequence is longitudinally disposed along the inner radial surface within the first portion 20 of the housing 14, i.e., directed perpendicularly into the page of the drawing figure.

The second permanent magnet and pole assembly 62 of the tangential actuator portion 30 further comprises (ii)(b) a second pole assembly 78 having a second set of pole members 80 arranged in a second radial configuration disposed about the spindle 24 on the first portion of the spindle. The second set of pole members 78 in the second radial configuration can include for example, a number of "$m_2$" poles, where "$m_2$" is an integer number. In one embodiment, the value of "$m_2$"="$n_2$" of the second sequence of individual S-N grouped magnet segments.

In addition, a free end radial surface of each pole member 80 of the second pole assembly 78 extends radially outward towards an inner radial surface of the second sequence 74 of individual S-N grouped magnet segments 76, proximate to, but separated by a gap from, the inner radial surface of the second sequence of individual S-N grouped magnet segments. Still further, in one embodiment, the outer radial surface of each pole member 80 complements an inner radial surface of an individual S-N grouped magnet segment 76, for example, as shown in FIG. 5(B).

According to one embodiment, the first pole assembly 70 is configured for operation between two distinct, different cogging positions determined as a function of the first sequence 66 of individual N-S grouped magnet segments, for example, as illustrated in FIGS. 4 and 5(A). In the first distinct cogging position, as shown in FIG. 4, the pole members 72 of the first pole assembly 70 are directed outwardly in a radial direction towards a free space (or gap) between adjacent individual N-S grouped magnet segments. In the second distinct cogging position, as shown in FIG. 5(A), the pole members 72 of the first pole assembly 70 are directed outwardly in a radial direction towards a center of an individual N-S grouped magnet segment. As a result, each distinct cogging position advantageously provides the tangential actuator portion with a different characteristic which can be used in creating at least two different functions in the personal care appliance 10. In other words, the distinct cogging positions of the tangential actuator of the present embodiments advantageously provide for different dynamic effects, and more particularly, the free space or gap between the individual N-S grouped magnet segments enables added power without added mass.

In addition, the second pole assembly 78 is configured for operation between two distinct, different cogging positions determined as a function of the second sequence 74 of individual N-S grouped magnet segments. In one embodiment, the two distinct, different cogging positions of the second pole assembly 78 are in radial alignment with the two distinct, different cogging positions of the first pole assembly 70. In another embodiment, the two distinct, different cogging positions of the second pole assembly 78 are in radial non-alignment with the two distinct, different cogging positions of the first pole assembly 70, for example, radial non-alignment for one cogging position as illustrated in FIGS. 5(A) and 5(B).

With reference again to FIG. 6, the tangential actuator portion 30 further comprises the electromagnetic coil 64 (or electromagnetic coil winding). The electromagnetic coil 64 is disposed about and coupled to the spindle 24 in-between the first and second magnet and pole assemblies, 70 and 78, respectively. Responsive to a rotation control signal applied to the electromagnetic coil 64 from the controller 34 (FIG. 2), the tangential actuator portion 30 rotationally displaces the spindle 24 with respect to the housing 14 about the principal axis 18, and thus imparting a desired rotational motion 26 to spindle 24. The desired rotational motion can comprise, for example, rotational motion having a peak-topeak amplitude with a range of 9-11°, or other range, as appropriate for a given actuator implementation. As indicated herein, the rotation and translation control signals can be configured to provide multiple different actuator motions and/or operational modes for the personal care appliance 10. For example, a preferred operation is an oscillating tangential motion near a resonant frequency. In addition, various arrangements of the first and second magnet and pole assemblies of the tangential actuator portion can be implemented to provide particular advantages. Different operating characteristics can be obtained in resonance if the two magnet and pole assemblies are cogged differently from each other.

Figure 7:
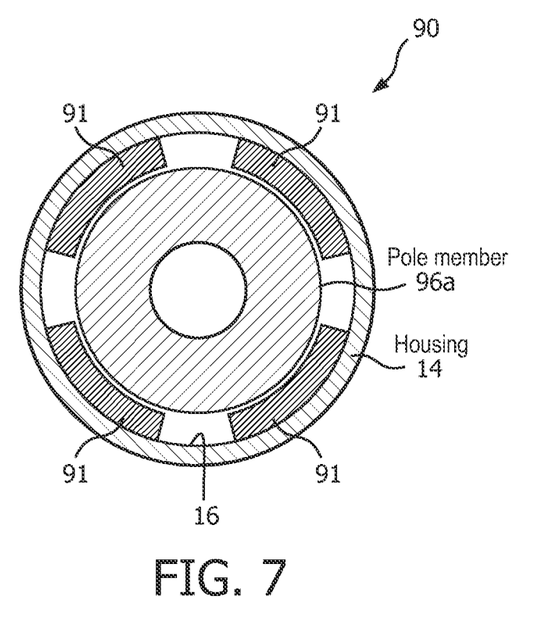
FIG. 7 is a cross-sectional view of a magnet and pole assembly of an axial actuator portion of the actuator according to an embodiment of the present disclosure.
Figure 8:
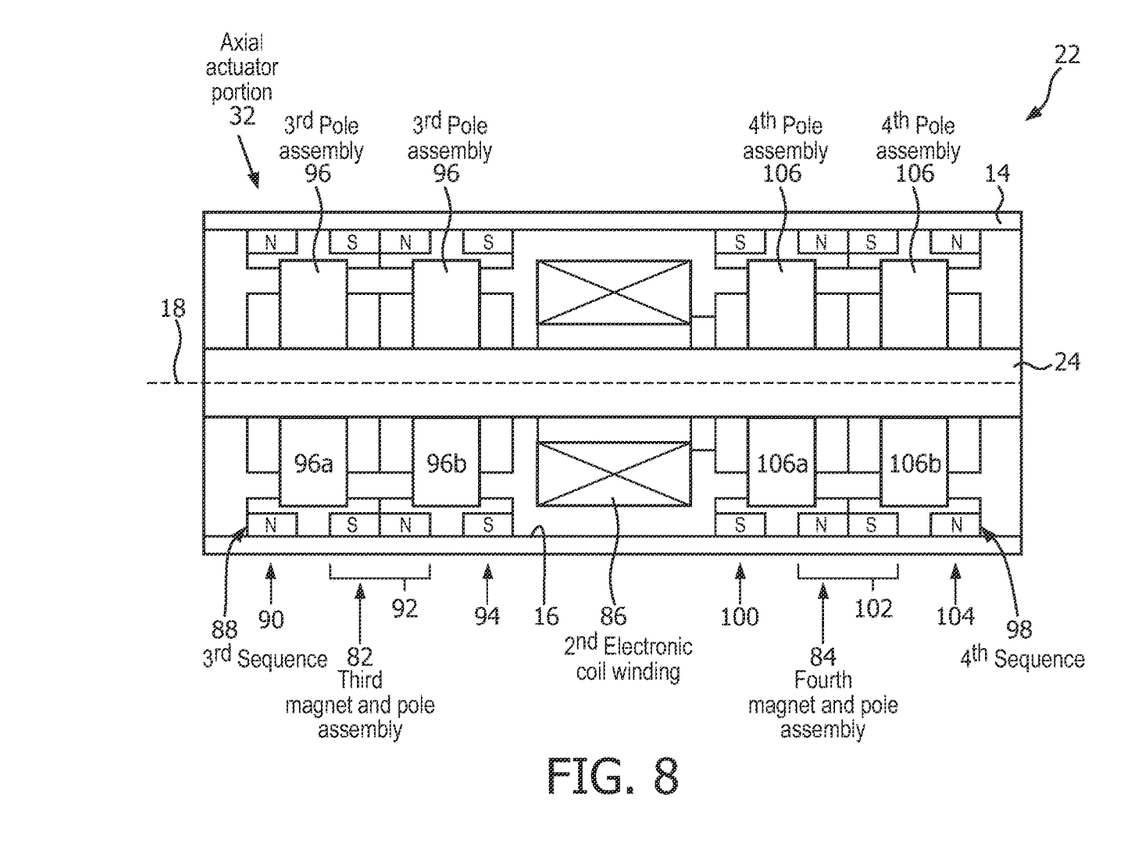
FIG. 8 is a cross-sectional view of the axial actuator portion, along its length dimension, of the actuator according to an embodiment of the present disclosure.

With reference now to FIGS. 7 and 8, a cross-sectional view of a magnet and pole assembly of an axial actuator portion (FIG. 7) and a cross-sectional view of the axial actuator portion (FIG. 8) of the actuator according to one embodiment of the present disclosure is shown. The axial actuator portion 32 is coupled between the second portion 22 (FIG. 2) of the housing 14 and the corresponding second portion of the spindle 24. The axial actuator portion 32 comprises (i) a third permanent magnet and pole assembly 82, (ii) a fourth permanent magnet and pole assembly 84 and (iii) an electromagnetic coil 86 (or electromagnetic coil winding).

The third permanent magnet and pole assembly 82 of the axial actuator portion 32 comprises (i)(a) a third sequence 88 of magnet segments (as indicated by reference numerals 90, 92 and 94 in FIG. 8) spaced apart in a first longitudinal orientation and having a third polarity order. The first longitudinal orientation and third polarity order can include, for example, a magnet segment 90, a free space, a second magnet segment 92, . . . , an $n_1^{th}$ free space, and $n_1^{th}$ magnet segment 94, where "$n_1$" is an integer number. As shown in FIG. 8, in one embodiment the integer number $n_1$ is equal to 3 (i.e., $n_1$=3), further wherein the longitudinal orientation comprises a predetermined spacing between adjacent ones of the magnet segments. However, "$n_1$" can represent any reasonable number of magnet segments configured for a given axial actuator portion implementation. In one embodiment, the intermediate magnet segments, such as segment 92, can comprise an individual N-S (or S-N) grouped magnet segment, as will be discussed further herein.

Each segment (e.g., segments 92, 94, 96) of the third sequence 88 of magnet segments is circumferentially disposed about the inner radial surface 16 within the second portion 22 of the housing 14 and at a respective longitudinal position along the length dimension of the housing. In other words, each segment is in the form of a ring about an inner periphery of the housing at a respective position along the length dimension of the housing. In one embodiment, segment 90 comprises an N-polarity magnet segment, segment 92 comprises an individual N-S grouped magnet segment, and segment 94 comprises an S-polarity magnet segment.

In addition, as illustrated in FIG. 7, segment 90 further comprises sub-segments 91 of a given magnetic polarity, for example, N-polarity. The sub-segments 91 are individual spaced apart sub-segments that collectively form segment 90 disposed about the inner radial surface 16. Segment 94 is similar to segment 90 and also comprises sub-segments that collectively form segment 94. With respect to segment 92, it also includes sub-segments similar to the sub-segments of the segments 90 and 94; however, each sub-segment of segment 92 comprises an individual N-S grouped magnet sub-segment. As illustrated in FIG. 8, an S-polarity portion of each individual N-S grouped magnet sub-segment of segment 92 is located to the right side of segment 90, while an N-polarity portion of each individual N-S grouped magnet sub-segment of segment 92 is located to the left side of segment 94.

In one embodiment, the number of sub-segments of each respective segment 90, 92 and 94 comprises four. The four sub-segments of each respective segment 90, 92 and 94 are equally spaced apart from one another about a given circumference, i.e., about the inner radial surface 16 of housing 14. In addition, the radial and axial dimensions of each respective sub-segment is determined according to the particular requirements of the given axial actuator portion 30. For example, each of the sub-segments can extend over radial distance of approximately 60° and the corresponding spacing between adjacent sub-segments can extend over a radial distance of approximately 30° for each respective segment 90, 92 and 94, for example, as shown in FIG. 7 with respect to sub-segments 91. Other sub-segment configurations are also possible.

The third permanent magnet and pole assembly 82 of the axial actuator portion 32 further comprises (i)(b) a third pole assembly 96 having a least one pole member disposed about the spindle 24 on the second portion of the spindle. As illustrated in FIG. 8, the third pole assembly 96 includes a first and second pole member, indicated by reference numerals 96a and 96b, respectively. In addition, the radial and axial dimensions of each respective pole member is determined according to the particular requirements of the given axial actuator portion 30. In one embodiment, each of the first and second pole members comprises a respective solid unitary pole member. In addition, each of the first and second pole members is longitudinally positioned between a given set of first and second magnet segments, corresponding to a respective longitudinal cogging position. For example, the first pole member 96a is positioned between segments 90 and 92, and the second pole member 96b is positioned between segments 92 and 94. As indicated above, segment 92 comprises an individual N-S grouped magnet segment. The individual N-S grouped magnet segment 92 is thus shared during operation of the axial actuator portion, i.e., alternating actuation between the first pole member 96a and the second pole member 96b.

Referring again to FIG. 8, the fourth permanent magnet and pole assembly 84 of the axial actuator 32 is similar to that of the third permanent magnet and pole assembly 82 with the following differences. The fourth permanent magnet and pole assembly 84 comprises (ii)(a) a fourth sequence 98 of magnet segments (as indicated by reference numerals 100, 102 and 104 in FIG. 8) spaced apart in a second longitudinal orientation and having a fourth polarity order, opposite to the third polarity order. The second longitudinal orientation and fourth polarity order can include, for example, a magnet segment 100, a free space, a second magnet segment 102, . . . , an $n_2^{th}$ free space, and $n_2^{th}$ magnet segment 104, where "$n_2$" is an integer number. As shown in FIG. 8, in one embodiment the integer number $n_2$ is equal to 3 (i.e., $n_2$=3), further wherein the longitudinal orientation comprises a predetermined spacing between adjacent ones of the magnet segments. However, "$n_2$" can represent any reasonable number of magnet segments configured for a given axial actuator portion implementation. In one embodiment, the intermediate magnet segments, such as segment 102, can comprise an individual N-S (or S-N) grouped magnet segment, as will be discussed further herein.

Each segment (e.g., segments 100, 102, 104) of the fourth sequence 98 of magnet segments is circumferentially disposed about the inner radial surface 16 within the second portion 22 of the housing 14. In other words, each segment is in the form of a ring about an inner periphery of the housing at a respective position along the length dimension of the housing. In one embodiment, segment 100 comprises an S-polarity magnet segment, segment 102 comprises an individual N-S grouped magnet segment, and segment 104 comprises an N-polarity magnet segment.

In addition, similarly to that illustrated with reference to FIG. 7 and discussed herein above, one or more of the segments 100, 102 and 104 can further comprises sub-segments of a respective magnetic polarity. The sub-segments are individual spaced apart sub-segments that collectively form a respective segment disposed about the inner radial surface 16 of housing 14. As illustrated in FIG. 8, an N-polarity portion of each individual N-S grouped magnet sub-segment of segment 102 is located to the right side of segment 100, while an S-polarity portion of each individual N-S grouped magnet sub-segment of segment 102 is located to the left side of segment 104.

In one embodiment, the number of sub-segments of each respective segment 100, 102 and 104 comprises four. The four sub-segments of each respective segment 100, 102 and 104 are equally spaced apart from one another about a given circumference, i.e., about the inner radial surface 16 of housing 14. In addition, the radial and axial dimensions of each respective sub-segment is determined according to the particular requirements of the given axial actuator portion 30. For example, each of the sub-segments can extend over radial distance of approximately 60° and the corresponding spacing between adjacent sub-segments can extend over a radial distance of approximately 30° for each respective segment 100, 102 and 104, for example, similarly as shown in FIG. 7 with respect to sub-segments 91. Other sub-segment configurations are also possible.

The fourth permanent magnet and pole assembly 84 of the axial actuator portion 32 further comprises (ii)(b) a fourth pole assembly 106 having a least one pole member disposed about the spindle 24 on the second portion of the spindle. As illustrated in FIG. 8, the fourth pole assembly 106 includes a first and second pole member, indicated by reference numerals 106a and 106b, respectively. In addition, the radial and axial dimensions of each respective pole member is determined according to the particular requirements of the given axial actuator portion 30. In one embodiment, each of the first and second pole members comprises a respective solid unitary pole member. In addition, each of the first and second pole members is longitudinally positioned between a given set of first and second magnet segments, corresponding to a respective longitudinal cogging position. For example, the first pole member 106a is positioned between segments 100 and 102, and the second pole member 106b is positioned between segments 102 and 104. As indicated above, segment 102 comprises an individual N-S grouped magnet segment. The individual N-S grouped magnet segment 102 is thus shared during operation of the axial actuator portion, i.e., alternating actuation between the first pole member 106a and the second pole member 106b.

In addition to the above, the free end radial surfaces of each pole member (e.g., 96a, 96b) of the third pole assembly 96 extends radially outward towards an inner radial surface of the third sequence 88 of magnet segments, proximate to, but separated by a gap from, the inner radial surface of the third sequence 88 of magnet segments. Furthermore, the free end radial surfaces of each pole member (e.g., 106a, 106b) of the fourth pole assembly 106 extends radially outward towards an inner radial surface of the fourth sequence 98 of magnet segments, proximate to, but separated by a gap from, the inner radial surface of the fourth sequence 98 of magnet segments.

With reference again to FIG. 8, the axial actuator portion 32 further comprises the electromagnetic coil 86 (or electromagnetic coil winding). The electromagnetic coil 86 is disposed about and coupled to the spindle 24 in-between the third and fourth magnet and pole assemblies, 82 and 84, respectively. Responsive to a translation control signal (or axial control signal) applied to the electromagnetic coil 86 from the controller 34 (FIG. 2), the axial actuator portion 32 axially displaces the spindle 24 with respect to the housing 14 along the principal axis 18, and thus imparting a desired axial motion 28 to spindle 24. The desired axial motion can comprise, for example, axial motion having a peak-to-peak amplitude up to 1 mm, or other range, as appropriate for a given actuator implementation. As indicated herein, the rotation and translation control signals can be configured to provide multiple different actuator motions and/or operational modes for the personal care appliance 10. For example, a preferred operation is an oscillating axial motion near a second resonant frequency. In addition, various arrangements of the third and fourth magnet and pole assemblies of the axial actuator portion can be implemented to provide particular advantages. Different operating characteristics can be obtained in resonance if the two magnet and pole assemblies are cogged differently from each other.

Figure 9:
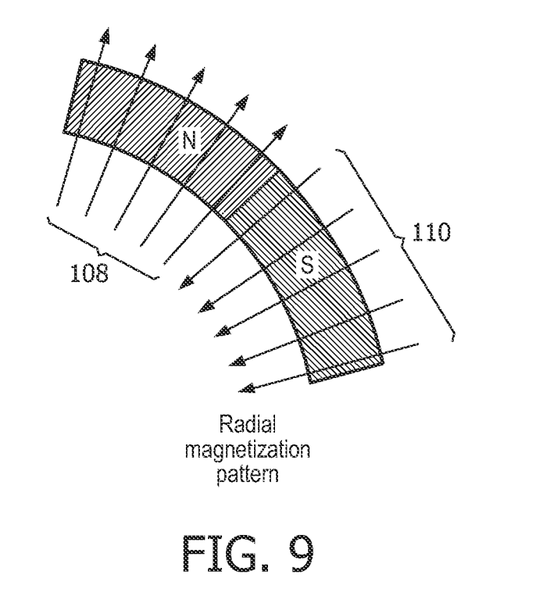
FIG. 9 is a diagrammatic view of a single N-S grouped magnet segment of the actuator having a radial N-S magnetization pattern according to an embodiment of the present disclosure.
Figure 10:
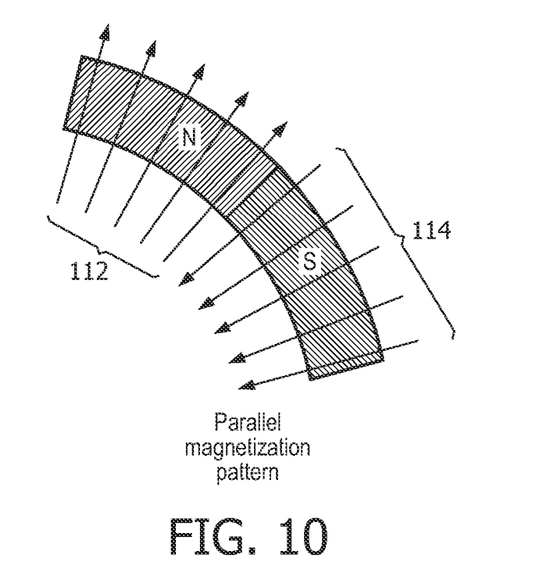
FIG. 10 is a diagrammatic view of a single N-S grouped magnet segment of the actuator having a parallel N-S magnetization pattern according to an embodiment of the present disclosure.

Referring now to FIG. 9, there is shown a diagrammatic view of a single N-S grouped magnet segment of the actuator having a radial N-S magnetization pattern according to an embodiment of the present disclosure. In addition, FIG. 10 illustrates a diagrammatic view of a single N-S grouped magnet segment of the actuator having a parallel N-S magnetization pattern according to another embodiment of the present disclosure. In connection with FIGS. 9 and 10, each individual N-S or S-N grouped magnet segment of the first and second sequence, 66 and 74 (FIG. 6), of individual N-S and S-N grouped magnet segments, 68 and 76 (FIG. 6), comprises a single magnet segment having a N-S or S-N magnetization pattern, respectively. As discussed herein, the magnets are combined pair wise (i.e., N-S or S-N). In this configuration, each N-S pair (or S-N pair) is made from one segment, and the N-S (S-N) magnetization pattern is created by a suitable magnetization process. Magnetization of the segments (e.g, the segments can comprise iron stators) can be accomplished after being mounted within the actuator housing. A boundary will be defined between N and S portions of each segment (or stator) via the magnetization process. In addition, a magnetic spring constant of the tangential actuator portion can be adjusted as appropriate for a given actuator implementation, depending on whether one or more of radial and/or parallel magnetization patterns are used.

In one embodiment, the respective N-S and S-N magnetization patterns each comprise a radial magnetization pattern, for example, as indicated by reference numerals 108 and 110 shown in FIG. 9. Regarding the radial magnetization pattern, the lines of magnetization are oriented in a radial direction with respect to a central axis, for example, corresponding with the principal axis 18. The N-polarity magnetization lines 108 are oriented radially outward, while the S-polarity magnetization lines 110 are oriented radially inward. In another embodiment, the respective N-S and S-N magnetization patterns each comprise a parallel magnetization pattern, for example, as indicated by reference numerals 112 and 114 shown in FIG. 10. Regarding the parallel magnetization pattern, the lines of magnetization are oriented parallel to one another in a given direction. The N-polarity magnetization lines 112 are parallel to one another and oriented outward, in a direction away from a central axis, while the S-polarity magnetization lines 114 are parallel to one another and oriented inward, in a direction towards a central axis.

Similarly, each individual N-S or S-N grouped magnet sub-segment of the individual S-N and N-S grouped magnet segments, 92 and 102 (FIG. 8), comprises a single magnet segment having a S-N or N-S magnetization pattern, respectively. The individual N-S or S-N grouped magnet sub-segments may also include a radial magnetization pattern or a parallel magnetization pattern, as discussed herein above with respect to the magnetization patterns of FIGS. 9 and 10.

Although several preferred embodiments have been described in detail above, those skilled in the art will readily appreciate that modifications are possible without materially departing from the novel teachings and advantages of the embodiments of the present disclosure. For example, the actuator housing can be a shape other than cylindrical. In addition, the axial actuator portion may comprise a single pole axial actuator. Furthermore, the embodiments of the present disclosure can be advantageously used in electrical tooth brushes, oral hygiene devices, teeth polishing devices, or other type of personal care appliance. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An actuator for a personal care appliance comprising:
   (a) a housing of magnetic material having an inner surface and a principal axis extending along a length dimension thereof, the housing further including at least first and second portions along the length dimension thereof;
   (b) a spindle of magnetizable material extending longitudinally within the housing along the principal axis, the spindle further including at least first and second portions corresponding with the at least first and second portions of the housing, respectively; and
   (c) a tangential actuator portion coupled between the first portion of the housing and the first portion of the spindle, wherein the tangential actuator portion comprises
   (i) a first magnet and pole assembly, wherein the first magnet and pole assembly comprises (i)(a) a first sequence of individual N-S grouped magnet segments spaced apart, via free space gaps, in a first radial orientation and having a first polarity order, each individual N-S grouped magnet segment of the first sequence including a single paired N and S magnet segment having a N-S magnetization pattern being longitudinally disposed along the inner surface within the first portion of the housing, and (i)(b) a first pole assembly having pole members arranged in a first radial configuration disposed about the spindle on the first portion of the spindle, wherein the first magnet and pole assembly is configured for operation between two distinct cogging positions, the first cogging position being substantially aligned with a first single individual N-S grouped magnet segment of the first sequence of individual N-S grouped magnet segments and the second distinct cogging position being substantially aligned between the first single individual N-S grouped magnet segment and a second individual N-S grouped magnet segment of the first sequence of individual N-S grouped magnet segments;
   (ii) a second magnet and pole assembly, wherein the second magnet and pole assembly comprises (ii)(a) a second sequence of individual N-S grouped magnet segments spaced apart via free space gaps, in a second radial orientation and having a second polarity order, opposite to the first polarity order, each individual N-S grouped magnet segment of the second sequence including a single paired N and S magnet segment having a N-S magnetization pattern being longitudinally disposed along the inner surface within the first portion of the housing, and (ii)(b) a second pole assembly having pole members arranged in a second radial configuration disposed about the spindle on the first portion of the spindle, and (iii) an electromagnetic coil disposed about and coupled to the spindle in between the first and second magnet and pole assemblies, wherein responsive to a rotation control signal applied to the electromagnetic coil, the tangential actuator portion rotationally displaces the spindle with respect to the housing about the principal axis.

2. The actuator of claim 1, further wherein the N-S magnetization pattern comprises one selected from the group consisting of (i) a radial magnetization pattern, and (ii) a parallel magnetization pattern.

3. The actuator of claim 1, wherein the second pole assembly is configured for operation between two distinct, different cogging positions determined as a function of the second sequence of individual N-S grouped magnet segments.

4. The actuator of claim 3, wherein the two distinct, different cogging positions of the second pole assembly are in radial alignment with the two distinct, different cogging positions of the first pole assembly.

5. The actuator of claim 3, wherein the two distinct, different cogging positions of the second pole assembly are in radial non-alignment with the two distinct, different cogging positions of the first pole assembly.

6. The actuator of claim 1, wherein the second radial orientation of the second sequence of individual N-S grouped magnet segments is offset from the first radial orientation of the first sequence of individual N-S grouped magnet segments, and
   wherein the second radial configuration of the second pole assembly is offset from the first radial configuration of the first pole assembly.

7. The actuator of claim 1, further comprising:
   an axial actuator portion coupled between the second portion of the housing and the second portion of the spindle, wherein the axial actuator portion comprises (i) a third magnet and pole assembly, wherein the third magnet and pole assembly comprises (i)(a) a third sequence of magnet segments spaced apart in a first longitudinal orientation and having a third polarity order, each segment of the third sequence of magnet segments being circumferentially disposed about the inner surface within the second portion of the housing, and (i)(b) a third pole assembly having at least one pole member disposed about the spindle on the second portion of the spindle, (ii) a fourth magnet and pole assembly, wherein the fourth magnet and pole assembly comprises (ii)(a) a fourth sequence of magnet segments spaced apart in a second longitudinal orientation and having a fourth polarity order, opposite to the third polarity order, each segment of the fourth sequence of magnet segments being circumferentially disposed about the inner surface within the second portion of the housing, and (ii)(b) a fourth pole assembly having at least one pole member disposed about the spindle on the second portion of the spindle, and (iii) a second electromagnetic coil disposed about and coupled to the spindle in-between the third and fourth magnet and pole assemblies, wherein responsive to a translation control signal applied to the second electromagnetic coil, the axial actuator portion axially displaces the spindle with respect to the housing along the principal axis.

8. The actuator of claim 7, wherein at least one segment of the third sequence of magnet segments further comprises a number of sub-segments of a same polarity spaced apart about a given circumference of the inner surface, and wherein at least one segment of the fourth sequence of magnet segments further comprises a number of sub-segments of a same polarity spaced apart about a given circumference of the inner surface.

9. The actuator of claim 8, further wherein the number of sub-segments of the third sequence of magnet segments comprises four sub-segments, and wherein the four sub-segments are equally spaced apart from one another about the given circumference, and further wherein the number of sub-segments of the fourth sequence of magnet segments comprises four sub-segments, and wherein the four sub-segments are equally spaced apart from one another about the given circumference.

10. The actuator of claim 7, wherein the third sequence of magnet segments further includes at least one individual N-S grouped magnet segment intermediate a first and last magnet segment in the third sequence of magnet segments, and wherein the third pole assembly further comprises at least two pole members disposed about the spindle on the second portion of the spindle, and wherein the fourth sequence of magnet segments further includes at least one individual N-S grouped magnet segment intermediate a first and last magnet segment in the fourth sequence of magnet segments, and wherein the fourth pole assembly further comprises at least two pole members disposed about the spindle on the second portion of the spindle.

11. The actuator of claim 10, further wherein the at least two pole members of the third pole assembly have axial cogging positions determined as a function of a position of the at least one individual N-S grouped magnet segment in the third sequence of magnet segments, and further wherein the at least two pole members of the fourth pole assembly have axial cogging positions determined as a function of a position of the at least one individual N-S grouped magnet segment in the fourth sequence of magnet segments.

12. The actuator of claim 7, further comprising: a controller for providing at least one selected from the group consisting of the rotation control signal, the translation control signal, and any combination of both rotation and translation control signals.

13. An actuator for a personal care appliance comprising:

(a) a housing of magnetic material having an inner radial surface and a principal axis extending along a length dimension thereof, the housing further including at least first and second portions along the length dimension thereof;

(b) a spindle of magnetizable material extending longitudinally within the housing along the principal axis, the spindle further including at least first and second portions corresponding with the at least first and second portions of the housing, respectively;

(c) a tangential actuator portion coupled between the first portion of the housing and the first portion of the spindle, wherein the tangential actuator portion comprises (i) a first magnet and pole assembly, wherein the first magnet and pole assembly comprises (i)(a) a first sequence of individual N-S grouped magnet segments spaced apart, via free space gaps, in a first radial orientation and having a first polarity order, each individual N-S grouped magnet segment of the first sequence including a single paired N and S magnet segment having a N-S magnetization pattern being longitudinally disposed along the inner radial surface within the first portion of the housing, and (i)(b) a first pole assembly having pole members arranged in a first radial configuration disposed about the spindle on the first portion of the spindle, wherein the first magnet and pole assembly is configured for operation between two distinct cogging positions, the first cogging position being substantially aligned with a first single individual N-S grouped magnet segment of the first sequence of individual N-S grouped magnet segments and the second distinct cogging position being substantially aligned between the first single individual N-S grouped magnet segment and a second individual N-S grouped magnet segment of the first sequence of individual N-S grouped magnet segments;

(ii) a second magnet and pole assembly, wherein the second magnet and pole assembly comprises (ii)(a) a second sequence of individual N-S grouped magnet segments spaced apart via free space gaps, in a second radial orientation and having a second polarity order, opposite to the first polarity order, each individual N-S grouped magnet segment of the second sequence including a single paired N and S magnet segment having a N-S magnetization pattern being longitudinally disposed along the inner radial surface within the first portion of the housing, and (ii)(b) a second pole assembly having pole members arranged in a second radial configuration disposed about the spindle on the first portion of the spindle, and (iii) an electromagnetic coil disposed about and coupled to the spindle in between the first and second magnet and pole assemblies, wherein responsive to a rotation control signal applied to the electromagnetic coil, the tangential actuator portion rotationally displaces the spindle with respect to the housing about the principal axis;

(d) an axial actuator portion coupled between the second portion of the housing and the second portion of the spindle, wherein the axial actuator portion comprises
(i) a third magnet and pole assembly, wherein the third magnet and pole assembly comprises (i)(a) a third sequence of magnet segments spaced apart in a first longitudinal orientation and having a third polarity order, each segment of the third sequence of magnet segments being circumferentially disposed about the inner radial surface within the second portion of the housing, and (i)(b) a third pole assembly having at least one pole member disposed about the spindle on the second portion of the spindle,
(ii) a fourth magnet and pole assembly, wherein the fourth magnet and pole assembly comprises (ii)(a) a fourth sequence of magnet segments spaced apart in a second longitudinal orientation and having a fourth polarity order, opposite to the third polarity order, each segment of the fourth sequence of magnet segments being circumferentially disposed about the inner radial surface within the second portion of the housing, and (ii)(b) a fourth pole assembly having at least one pole member disposed about the spindle on the second portion of the spindle, and
(iii) a second electromagnetic coil disposed about and coupled to the spindle in-between the third and fourth magnet and pole assemblies, wherein responsive to a translation control signal applied to the second electromagnetic coil, the axial actuator portion axially displaces the spindle with respect to the housing along the principal axis; and
(e) a controller for providing at least one selected from the group consisting of the rotation control signal, the translation control signal, and any combination of both rotation and translation control signals.

14. The actuator of claim 13, wherein the third sequence of magnet segments further includes at least one individual N-S grouped magnet segment intermediate a first and last magnet segment in the third sequence of magnet segments, and wherein the third pole assembly further comprises at least two pole members disposed about the spindle on the second portion of the spindle, further wherein the at least two pole members have axial cogging positions determined as a function of a position of the at least one individual N-S grouped magnet segment in the third sequence of magnet segments, and wherein the fourth sequence of magnet segments further includes at least one individual N-S grouped magnet segment intermediate a first and last magnet segment in the fourth sequence of magnet segments, and wherein the fourth pole assembly further comprises at least two pole members disposed about the spindle on the second portion of the spindle, further wherein the at least two pole members have axial cogging positions determined as a function of a position of the at least one individual N-S grouped magnet segment in the fourth sequence of magnet segments.

* * * * *